(12) United States Patent
Cerda

(10) Patent No.: US 8,476,414 B2
(45) Date of Patent: Jul. 2, 2013

(54) SUBSTRATES AND INTERNAL STANDARDS FOR MASS SPECTROMETRY DETECTION

(75) Inventor: Blas Cerda, Milford, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 356 days.

(21) Appl. No.: 12/210,262

(22) Filed: Sep. 15, 2008

(65) Prior Publication Data

US 2009/0068634 A1 Mar. 12, 2009

Related U.S. Application Data

(63) Continuation-in-part of application No. PCT/US2007/063894, filed on Mar. 13, 2007.

(60) Provisional application No. 60/781,855, filed on Mar. 13, 2006.

(51) Int. Cl.
*C07H 15/10* (2006.01)
*C07H 15/203* (2006.01)
*C12Q 1/54* (2006.01)
*C12Q 1/34* (2006.01)

(52) U.S. Cl.
USPC ............. 536/17.9; 514/25; 435/14; 435/18

(58) Field of Classification Search
USPC ................ 536/17.9; 514/25; 435/14, 18
See application file for complete search history.

(56) References Cited

U.S. PATENT DOCUMENTS

| | | | | |
|---|---|---|---|---|
| 4,968,785 | A | * | 11/1990 | Moser et al. ............. 536/4.1 |
| 5,384,334 | A | * | 1/1995 | Polovsky et al. ......... 514/777 |
| 6,852,544 | B2 | | 2/2005 | Aebersold et al. |

OTHER PUBLICATIONS

Deschavanne et al., J. Biol. Chem., 1978, 253(3), p. 833-837.*
Czjzek et al., PNAS, 2000, 97(25), p. 13555-13560.*
Erickson et al., J. Lipid Res. 1973, 14, p. 133-137.*
Rozaklis, Tina et al., "Determination of Oligosaccharides in Pompe Disease by Electrospray Ionization Tandem Mass Spectrometry", Clinical Chemistry 48:1, pp. 131-139 (2002).
Umapathysivam, Kandiah et al., "Determination of Acid x-Glusosidase Protein: Evaluation as a Screening Marker for Pompe Disease and Other Lysosomal Storage Disorders", Clinical Chemistry 46:9, pp. 1318-1325 (2000).
Chace, Donald H., et al., "Use of Tandem Mass Spectrometry for Multianalyte Screening of Dried Blood Specimens from Newborns", Clinical Chemistry 49:11, 1797-1817 (2003).
Li, Yijun, et al., "Direct Multiplex Assay of Lysosomal Enzymes in Dried Blood Spots for Newborn Screening", Clinical Chemistry 50:10, pp. 1785-1796 (2004).
Okumiya T et al.; A New Diagnostic Assay for Glycogen Storage Disease Type II in Mixed Leukocytes; Molecular Genetics and Metabolism; Academic Press; San Diego, CA, vol. 88; No. 1; Dec. 2005; pp. 22-28.
Michael H. Gelb et al.; Direct Multiplex Assay of Enzymes in Dried Blood Spots by Tandem Mass Spectrometry for the Newborn Screening of Lysosomal Storage Disorders; Journal of Inherited Metabolic Disease; Kluwer Academic Publishers; DO., vol. 29, No. 2-3; Jul. 2005; pp. 397-404; XP019392093.
Li Yijun et al.; Direct Multiplex Assay of Lysosmal Enzymes in Dried Blood Spots for Newborn Screening; Clinical Chemistry, American Association for Clinical Chemistry; Washington, D.C. vol. 50, No. 10; pp. 1785-1796; XP002514511, Pub Date: 2004.

* cited by examiner

*Primary Examiner* — Shaojia Anna Jiang
*Assistant Examiner* — Jonathan S Lau
(74) *Attorney, Agent, or Firm* — Gifford, Krass, Sprinkle, Anderson & Citkowski, P.C.

(57) ABSTRACT

An inventive substrate is provided which includes a substrate compound of formula $A—B^1—B^2—B^3$: wherein A is a sugar moiety; $B^1$ is a linker moiety allowing the conjugation of moiety A and the remaining structure of the substrate; $B^2$ contains a permanently charged element such as a quaternary ammonium group so as to increase proton affinities and ionization efficiencies for mass spectrometry detection efficiencies analysis; and $B^3$ of various carbon length conferring specificities to targeted enzymes. Also provided is a process to detect lysosomal diseases by contacting a sample with the inventive substrate along with an internal standard which is isotope-labeled analog of the product cleaved by a targeted enzyme upon the substrate.

15 Claims, 11 Drawing Sheets

Scheme representing the enzymatic hydrolysis of the inventive substrate.

Substrate, Product B and Internal Standards for Product B are measured simultaneously by tandem mass spectrometry Internal Standard for Product B

SUBSTRATES AND INTERNAL STANDARDS FOR MASS SPECTROMETRY DETECTION

CROSS-REFERENCE TO RELATED APPLICATIONS

This application is a continuation in part of PCT/US2007/063894 filed Mar. 13, 2007, which in turn claims priority to U.S. Provisional Patent Application Ser. No. 60/781,855, filed Mar. 13, 2006. The contents of these priority documents are incorporated herein by reference.

FIELD OF THE INVENTION

The present invention relates to reagents and related methods for detecting and/or quantifying enzyme activities in a sample. More specifically, the present invention relates to reagents and methods for detecting and/or quantifying the activity of one or more lysosomal enzymes in a sample using mass spectrometry.

BACKGROUND OF THE INVENTION

Lysosomal storage diseases are a group of inherited disorders characterized by deficiencies in specific enzymes in the body, which results in the body's inability to break down metabolic substances. As an example, Fabry disease is a lysosomal storage disorder seen in one out of every 40,000 people. It is caused by a deficiency in the enzyme alpha-galactosidase which then results in the body's inability to break down specific fatty substances called globotriaosylceramide. A second example is Gaucher disease, a lysosomal storage disease caused by an inability to break down fatty substances or lipids called glucosylceramides (also called glucocerebrosides). Individuals with Gaucher disease do not make glucocerebrosidase, an enzyme that is needed to break down these fatty substances. These fatty substances then accumulate in cells of the liver, spleen, and bone marrow. A third example is Pompe disease, a lysosomal storage disorder caused by a deficiency in the enzyme acid alpha-glucosidase which is needed to break down certain sugars called glycogen. When the enzyme acid alpha-glucosidase is missing, glycogen accumulates in various tissues and organs in the body.

These diseases are, for the most part, childhood disorders. In most of them, patients are normal at birth and have progressive neurological deterioration beginning at some later time. In some of them, the disease is manifested in adulthood. The clinical phenotype depends on the type and severity of the biochemical defect. Some of these lysosomal disorders, such as Pompe disease and Krabbe disease, manifest primarily in infancy. Therefore, there have been ongoing efforts in developing methods to detect these disorders before the onset of clinical symptoms so that therapeutic interventions can be initiated.

Over the past decade laboratories that test for metabolic disorders have introduced tandem mass spectrometry into their newborn screening programs. Tandem mass spectrometry continues to gain popularity in the clinic because this technology allows for assay of many metabolites in a single sample. For example, this technology has been implemented as a routine clinical practice for the detection of hereditary metabolic disorders in newborns using dry blood spot samples (Schulze A et al., Pediatrics 2003; 111:1399-406). Although lysosomal enzyme activities can be quantified using tandem mass spectrometry (Gelb M H et al., Clinical Chemistry 50:10, 1785-1796, 2004), published assay methods have not been readily adaptable to a clinical setting due to cumbersome procedures and harsh assay components such as chloroform.

Thus, there is a continuing need for improving the methods and compositions for detecting lysosomal diseases.

SUMMARY OF THE INVENTION

Improved compositions and processes for detecting enzymatic reactions using mass spectrometry are provided according to embodiments of the present invention.

An inventive substrate has the general formula of $$A\text{—}(B^1\text{—}B^2\text{—}B^3) \quad (I)$$

and an isotopically labeled product internal standard of formula $$(B^1\text{—}B^2\text{—}B^3) \quad (II)$$

where A is a monosaccharide or a disaccharide and $B^1$ is a $C_1$-$C_{20}$ alkyl, an N or S substituted $C_6$-$C_{20}$ aryl, $C_6$-$C_{20}$ heterocyclic containing a heteroatom of N, O or S; $B^2$ is

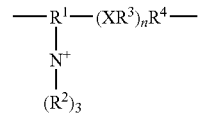

where $R^1$ is a $C_1$-$C_{20}$ alkyl; $C_4$-$C_{20}$ ether; $C_1$-$C_{20}$ alkyl having a substituent of N, O, or S; an N, O or S heteroatom substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ alkyl, a $C_2$-$C_{20}$ alkyl having a substituent of $C_1$-$C_{20}$ alkyl; X is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^3$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

A process for mass spectrometric analysis of an enzyme includes contacting the enzyme with a substrate of Formula I to generate a cleavage product $B^1$—$B^2$—$B^3$ that has a cleavage product molecular weight upon enzymatic reaction. An internal standard is provided $(B^1\text{—}B^2\text{—}B^3)'$ with the substrate of Formula I, where $(B^1\text{—}B^2\text{—}B^3)'$ has at least one stable secondary prevalence isotope of molecular weight different than the cleavage product molecular weight and $B^1$, $B^2$, and $B^3$ of $(B^1\text{—}B^2\text{—}B^3)'$ have the identities of $B^1$, $B^2$, and $B^3$ of the Formula I substrate. Mass spectrometric analysis quantifies the mass-to-charge ratio between the cleaved product and the internal standard and thereby the enzymatic activity. Particular enzymes of interest in lysosomal storage disease include acid α-galactosidase A, acid β-glucocerebrosidase, galactocerebroside α-galactosidase, acid sphingomyelinase, and acid α-glucosidase. Structurally identical cleavage product $(B^1\text{—}B^2\text{—}B^3)$ and internal standard $(B^1\text{—}B^2\text{—}B^3)'$ that differ only in molecular weight are preferred.

A commercial package is disclosed inclusive of a Formula I substrate, an internal standard $(B^1\text{—}B^2\text{—}B^3)'$ that includes a stable secondary prevalence isotope and differs in molecular weight relative to $B^1$—$B^2$—$B^{3'}$ of substrate Formula I. Instructions are provided for detecting activity of an enzyme recognizing Formula I substrate in a sample by mass spectrometric analysis.

A process for mass spectrometric analysis of an enzyme includes labeling an enzymatic first substrate of Formula I with an isotopic label L1 to yield $^{L1}(A)$—$^{L1}(B^1$—$B^2$—$B^3)$ and a second substrate of Formula I with a different isotopic label L2 to yield $^{L2}(A)$—$^{L2}(B^1$—$B^2$—$B^3)$. Combining $^{L1}(A)$—$^{L1}(B^1$—$B^2$—$B^3)$ and $^{L2}(A)$—$^{L2}(B^1$—$B^2$—$B^3)$ with the enzyme to allow for cleavage of the first and second substrates. By quantifying an increase in cleavage products $^{L1}(A)$, $^{L1}(B^1$—$B^2$—$B^3)$, $^{L2}(A)$, and $^{L2}(B^1$—$B^2$—$B^3)$ and a decrease in the first and second substrates by mass spectrometry, enzyme activity is analyzed. The process of mass spectrometric analysis described is particularly well suited for detection of a lysosomal storage disease, alone or simultaneous with the detection of a second lysosomal storage device.

An inventive process is provided which includes incubating a sample with an assay solution containing an inventive substrate and an inventive internal standard and subjecting the resulting sample to mass spectrometry analysis.

DETAILED DESCRIPTION OF THE PREFERRED EMBODIMENTS

Figure 1:
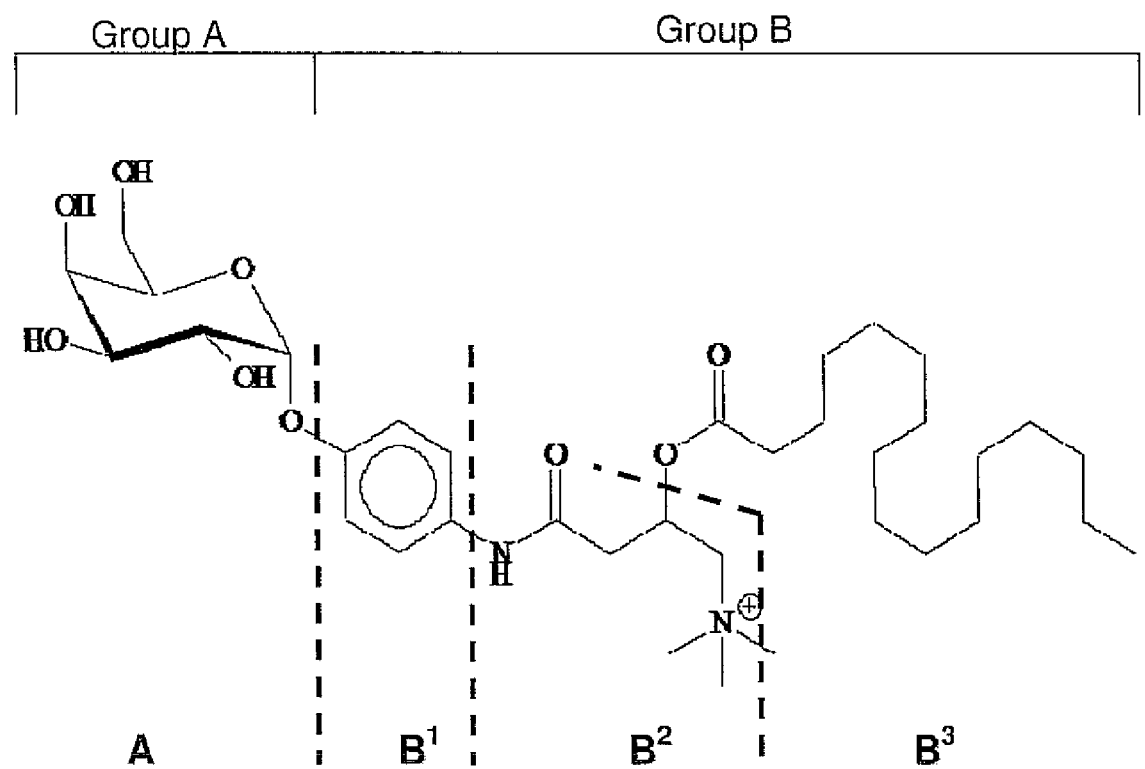
FIG. 1 is an exemplary substrate structure for detecting lysosomal storage diseases.

The present invention has utility as an analytical reagent composition for detecting lysosomal storage disorders. Through the application of substrates and internal standards that are readily dissolvable in solutions adaptable for mass spectrometry analysis, detecting abnormal enzyme activities associated with lysosomal storage diseases is more practical and less cumbersome.

The present invention relates to substrates that are targeted for lysosomal enzymes including: acid α-galactosidase A (GLA), acid β-glucocerebrosidase (ABG), galactocerebroside α-galactosidase (GALC) acid α-glucosidase (GAA). The action of these enzymes over the substrates is used to measure the corresponding enzyme activities in a sample and thus these substrates are used to detect the following lysosomal storage disorders: Fabry (GLA), Gaucher (ABG), Krabbe (GALC) and Pompe (GAA).

An inventive substrate has the general formula of A—$(B^1$—$B^2$—$B^3)$ where A is a monosaccharide or a disaccharide and $B^1$ is a $C_1$-$C_{20}$ alkyl, an N or O substituted $C_6$-$C_{20}$ aryl, $C_6$-$C_{20}$ heterocyclic containing a heteroatom of N, O or S; $B^2$ is

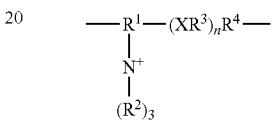

where $R^1$ is a $C_1$-$C_{20}$ alkyl; $C_4$-$C_{20}$ ether; $C_1$-$C_{20}$ allyl having a substituent of N, O, or S; an N, O, or S heteroatom substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ allyl, a $C_2$-$C_{20}$ allyl having a substituent of $C_1$-$C_{20}$ alkyl; K is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $B^3R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^3$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

The specificity of the substrate for a particular lysosomal enzyme is provided in part by structural variations in the sugar moiety A such as A being a monosaccharide or a disaccharide. Exemplary sugar moieties include α-D-glucose for detecting the Pompe disease; β-D-glucose for detecting the Gaucher disease; α-D-galactose for detecting the Fabry disease; and β-D-galactose for detecting the Krabbe disease. Furthermore, the specificity of the substrate during the mass spectrometry analysis is also conferred by variations in the carbon length and degree of saturation within the fatty-acyl group of $B^3$. Exemplary chemical structures of $B^3$ include a twelve-carbon fatty-acyl group specific for detecting the Pompe disease; a fourteen-carbon fatty-acyl group specific for detecting the Gaucher disease; a sixteen-carbon fatty-acyl group specific for detecting the Fabry disease; and an eighteen-carbon fatty-acyl group specific for detecting the Krabbe disease.

$B^1$ is a linker moiety which functions to allow conjugation of the sugar moiety A to the remaining structure of the substrate. $B^1$ also functions as a spacer between the sugar moiety A and the remaining structure of the substrate so as to provide flexible access for a target enzyme.

A quaternary ammonium group is a feature of $B^2$. The group carries a permanent positive charge. Upon an enzymatic reaction, a cleaved product of $B^1$—$B^2$—$B^3$ carries with enhanced increased sensitivity due to the presence of the quaternary ammonium group located on the $B^2$. This property results in high signal in the tandem mass spectrometry analysis and less limitations in the over all assay. Additionally, the permanent charge makes the inventive substrate more soluble in aqueous buffers so as to avoid the need for the use of very non-polar solvents such as chloroform. In comparison to prior art substrates, the substrate according to the present invention is more hydrophilic and requires less or no detergents. This is advantageous since like the use of chloroform, the use of detergents demands cumbersome clean-up steps including the labor-intensive liquid-liquid and solid phase extractions.

The substrate is structurally terminated by a $B^3$ group. As mentioned above, $B^3$ is structurally tailored to provide specificity during the mass spectrometry analysis by conferring different carbon length and or degree of saturation of carbon chain. Therefore, very similar substrates are synthesized with changes in their molecular mass that are differentiable by the mass spectrometry analysis.

Thus, as it is envisioned in the present invention, one can synthesize substrates with four different sugars, each specific to a particular lysosomal enzyme, and each having a slightly different chain length in subgroup $B^3$. The variation in mass thus allows the identification by mass spectrometry of each of the four substrates and corresponding enzymatic products in cases in which the substrates are used in a multiplex assay where two or more are analyzed in the same sample or in the same tube or well of a microtiter plate. This composition thus allows for a single synthesis scheme. In the prior art each substrate requires a unique synthetic pathway. Having a common synthesis pathway for two or more of these substrates can mean significant savings in production environments due to shorter and less complex production processes and the use of common raw materials.

For detecting Pompe disease, an exemplary sugar moiety is α-D-glucose and an exemplary $B^1$—$B^2$—$B^3$ portion is 4-aminophenyl-carnitinyl-alkyl chain with $B^3$ of 10-20 carbons in length and preferably of 12 carbons in length. For detecting Gaucher disease, an exemplary sugar moiety is β-D-glucose and an exemplary $B^1$—$B^2$—$B^3$ portion is 4-aminophenyl-carnitinyl-alkyl with $B^3$ of 10-20 carbons in length and preferably of 14 carbons in length. For detecting Fabry disease, an exemplary sugar moiety is α-D-galactose and an exemplary $B^1$—$B^2$—$B^3$ portion is 4-aminophenyl-carnitinyl-alkyl with $B^3$ of 10-20 carbons in length and preferably is of 16 carbons in length. For detecting Krabbe disease, an exemplary sugar moiety is β-D-galactose and an exemplary B portion is 4-aminophenyl-carnitinyl-alkyl with $B^3$ of 10-20 carbons in length and preferably is of 18 carbons in length.

The present invention also relates to internal standards designed to measure against the amount of products with general formula of $B^1$—$B^2$—$B^3$ cleaved from the inventive substrates upon enzymatic reactions. Internal standards are structurally identical to the cleaved products except that the internal standards differ in mass-to-charge (m/z) ratio than the cleaved products by a modification step including isotopic labeling. The internal standards of the present invention are therefore stable isotope-labeled analogs of the cleaved products where one or more atoms are replaced by corresponding atomic isotopes so as to create a shift in the mass. An example of such labeling is the replacement of $^1H$ on an acyl group of $B^3$ with $^2D$. As a result, a "heavier" internal standard molecule with the substituted $^2D$ reveals a different m/z on the mass spectrometry spectra results than a cleaved product would normally reveal. The shift in mass is employed to identify the cleaved products from the internal standards in the mass spectrometry experiment.

In one particular embodiment, a $B^1$ subgroup of an inventive substrate is a substituted amino phenyl group.

In another particular embodiment, a combined $B^2$—$B^3$ subgroup is an acylcarnitine with a positively charged quaternary ammonium moiety and the acyl tail is of carbon length from 12 to 18.

In another particular embodiment, an internal standard is labeled with deuterium to cause a mass change of 3 to 9 Daltons from the corresponding cleaved product.

In another particular embodiment, an inventive substrate specific for detecting the Krabbe disease has a group A of β-D-galactose, a group $B^1$ of a methyl, a group $B^2$ of a amidyl terminating with a quaternary ammonium, and group $B^3$ of alkenyl alcohol with a carbon length of 12 to 20.

In yet another particular embodiment, an inventive substrate specific for detecting the Gaucher disease has a group A of β-D-glucose, a group $B^1$ of a methyl, a group $B^2$ of a amidyl terminating with a quaternary ammonium, and group $B^3$ of alkenyl alcohol with a carbon length of 12 to 20.

The present invention also relates to methods to measure the activities of targeted lysosomal enzymes in a sample. The sample includes that of serum, plasma, whole blood, urea, saliva, or other biological fluids or tissue lysates. The sample is deposited and dried on a filter paper matrix. A portion of the filter paper sample is then excised and deposited in an assay tube or micro titer plate well to which an assay solution is added. The assay solution comprises aqueous buffers, a substrate and an internal standard as well as required inhibitors such as ones for competing glycosidases. The sample mixture is then incubated for a determined period of time in the range of 4 to 24 hours and at a particular temperature. Once incubation is complete, the enzymatic reaction is terminated by adding a solution that acts to precipitate the enzymes. An exemplary type of the solution includes alcohol, acetonitrile or dilute trifluoro acetic acid. A portion of the incubation mixture is transferred to a new assay vessel to which is added a neat solution such as methanol, acetonitrile, water-methanol mixtures or water-acetonitrile. Other types of neat solutions are selected by those skilled in the art to be compatible with tandem mass spectrometry analysis. The test sample so diluted by an aliquot of neat solution reduces the amount of endogenous competing material so as to relatively increase the sensitivity of the tandem mass spectrometry analysis. The diluted sample is directly injected without further modification into the tandem mass spectrometer either manually or automatically with the aid of autosamplers and liquid handlers. The tandem mass spectrometer is set to simultaneously detect the added substrate, the corresponding resulting enzymatic product and the corresponding internal standards. Such detection is accomplished by means of parent ion scans, precursor ion scans or multiple reaction monitoring scans. The tandem mass spectrometer is set to detect one or more substrates, products and corresponding internal standards. The relative abundance of the observed products and corresponding internal standards is used to quantitate the corresponding enzyme activity.

Samples that are analyzable by methods of the present invention include, but are not limited to, tissue homogenates; cell culture lysates; biological fluids including urine, blood in liquid or dry form, tears, saliva, and cerebrospinal fluid; biological mixtures containing proteins, lipids, carbohydrates, and nucleic acids. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize chances in the molecules in the sample. Such inhibitors include, for example, chelators such as ethylenediamine tetraacetic acid (EDTA), ethylene glycol bis(P-aminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. For use in the methods described herein, a sample can be in a variety of physical states. For example, a sample can be a liquid or solid, can be dissolved or suspended in a liquid, can be in an emulsion or gel, and can be absorbed onto a material. As a non-limiting example, a sample can be a liquid blood sample, liquid serum sample, liquid white blood cell sample, dried blood, serum, or white cell sample, or such a sample absorbed onto a paper or polymer substrate. Prior to performing mass spectrometry, a sample can be extracted. For the methods described herein, a sample (e.g., an extracted sample) does not require further chemical modification prior to analysis using tandem mass spectrometry, although such modification can be performed if desired.

Samples in the form of a dry blood spot are commonly used when screening blood from newborns and children patients. For these patient subjects, blood collected and retained on a filter paper is a laboratory specimen that is readily collectable and easily stored. A sample on a filter paper can be eluted before incubating with the assay solution. The step of eluting is to release proteins from the dry filter paper into an aqueous solution which contains a water-based buffer such as phosphate buffer, saline and a protease inhibitor. The protease inhibitor can, for example, include one or more of the following: AEBSF hydrochloride in a final concentration of 50 to 400 µg/ml, EDTA disodium dehydrate in a final concentration of 0.2 to 25 mg/ml, leupeptin hemisulfate in a final concentration of 0.5 to 1 µg/ml, and pepstatin A in a final concentration of 0.5 to 1 µg/ml. The elution can be carried out over a period of 20 to 60 minutes depending on the size of specimen used and can be facilitated with vertical or horizontal shaking. Liquid extracts can then be transferred manually or by automated liquid handling devices to tubes or micro-titer plates.

With or without being first solubilized as described above, the dry blood sample is incubated in an assay solution. In particular, the assay solution is water based. The assay solution contains a suitable buffer such as phosphate buffered saline, a suitable protease inhibitor such as one to compete glycosidase, a substrate that is labeled with an isotope, and an internal standard that is labeled with a different isotope. The protease inhibitor includes one or more of the following: inhibitor for glycosidase, AEBSF hydrochloride in a final concentration of 50 to 400 µg/ml, EDTA disodium dehydrate in a final concentration of 0.2 to 25 mg/ml, leupeptin hemisulfate in a final concentration of 0.5 to 1 µg/ml, and pepstatin A in a final concentration of 0.5 to 1 µg/ml. During the incubation period, the substrate is cleaved by an enzyme of interest from the dry blood sample to form respective products.

In one aspect, the incubation reaction is terminated by an addition of pure alcohol, acetonitrile or diluted trifluoro acetic acid. The products formed from the enzymatic reaction is rather polar mainly due to the built-in positively charged moiety such as a quaternary ammonium cation, therefore there remains no need to use a non-polar solvent such as chloroform to terminate the enzymatic reaction and to keep the products in solution. Due to the intricacy of the MS/MS system, samples that are eventually subject to the MS/MS system need to be in a solvent that is not "hostile" to the MS/MS system. For example, such solvent should not be detergent based, nor should it contain corrosive agents such as chloroform. Pure ethanol or pure methanol is preferred simply because it is easily vaporized upon entering the ionization source of the mass spectrometer.

For each enzyme to be detected, a set of specific substrate and an internal standard is contained within the assay solution. The assay solution is designed as unique and specific for the detection of a particular enzyme; alternatively, it is so designed to be adaptable and universal for the concurrent detection of multiple enzymes. The incubation is carried out in individual tubes, vials, or with a multi-well filter plate such as a 96-well or 386-well filter plate.

The required size of a sample varies with the number of enzymes to be tested. Practically, for the analysis of single enzyme, a dry blood spot specimen on a filter paper in a size of 1-3 mm is commonly used. More sample is typically used when the enzyme to be analyzed has a relatively low presence in the specimen since no multiple enzymatic extraction is required in the case of single analyte analysis. Alternatively, enzymes that are of relatively high expression levels and or enzymatic activities are analyzed concurrently out of one sample in a greater quantity.

Substrates for a selected protein of interest are of natural or synthetic origin. The protein of interest is composed of an enzyme that is associated with a disease state or birth defect or one that is routinely assayed for medical purposes. Enzyme substrate of interest include acid α-galactosidase A, acid β-glucocerebrosidase, acid galactocerebroside α-galactosidase, acid sphingomyelinase, and acid α-glucosidase.

An inventive composition of the general formula of A—$B^1$—$B^2$—$B^3$ is hydrophilic in a solvent such as pure methanol or pure ethanol. A is a monosaccharide or a disaccharide. $B^1$ is a linker arm, $B^2$ contains a quaternary ammonium cation that is permanently positively charged, and $B^3$ is long carbon tail. The type of A moiety or the length of the allyl chain in the $B^1$—$B^2$—$B^3$ moiety differs according to the target enzyme examined. The linker arm $B^1$ is designed so as to confer relatively hydrophilic characteristics. Particularly, the linker arm $B^1$ has a hydrophenol structure. The $B^1$—$B^2$—$B^3$ moiety in nature is hydrophilic to ensure good solubility of the substrate, and it has basic groups such as a permanently positively charged quaternary ammonium cation which are efficiently protonated by ESI and thus ensure sensitive detection by mass spectrometry.

In one embodiment, the invention provides a reagent of formula A—$B^1$—$B^2$—$B^3$ wherein A is a monosaccharide or a disaccharide and preferably an aldohexose or a ketohexose; $B^1$ is a phenol, a nitrophenol, or a phenyl ester such as a phenyl benzoate; $B^2$ contains a pendent quaternary ammonium cation extending from structure that prior to condensation to $B^1$ alone or also with a $B^3$ tail is carnitine,

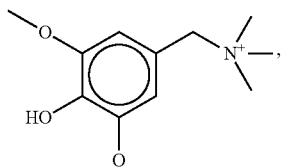

(AV29285L 800, ARVI Co. Ltd., Yerevan, Armenia)

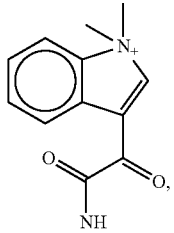

(Pubchem No. 3833216)

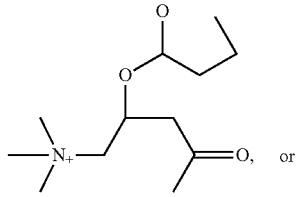  or (Pubchem No. 786970, CAS 25518-46-1)

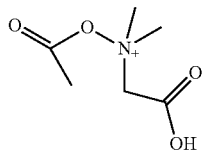

(Chembank 1271)

A is a monosaccharide or a disaccharide and $B^1$ is a $C_1$-$C_{20}$ alkyl, an N or O substituted $C_6$-$C_{20}$ aryl, $C_6$-$C_{20}$ heterocyclic containing a heteroatom of N, O or S; $B^2$ is

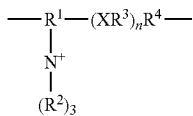

where $R^1$ is a $C_1$-$C_{20}$ alkyl; $C_4$-$C_{20}$ ether; $C_1$-$C_{20}$ alkyl having a substituent of N, O, or S; an N, O or S heteroatom substituted $C_6$-$C_{20}$ aryl, $C_6$-$C_{20}$ heterocyclic containing a heteroatom of N, O or S; $R^2$ is independently in each occurrence a H, a $C_1$-$C_{20}$ alkyl, a $C_2$-$C_{20}$ alkyl having a substituent of $C_1$-$C_{20}$ alkyl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; $R^2$ is independently in each occurrence a H, a $C_1$-$C_{20}$ alkyl, a $C_2$-$C_{20}$ alkyl having a substituent of $C_1$-$C_{20}$ alkyl; X is independently in each occurrence a nullity, oxygen, sulfur, or nitrogen; $R^3$ is independently in each occurrence a nullity, $C_1$-$C_{20}$ alkyl, $C_1$-$C_{20}$ having a substituted $C_6$-$C_{20}$ aryl, $C_6$-$C_{20}$ heterocyclic containing a heteroatom of N, O or S; n is an integer between 0 and 30, inclusive; $B^3R^4$ is independently in each occurrence a nullity, $C_1$-$C_{20}$ alkyl, $C_1$-$C_{20}$ having a substituted $C_6$-$C_{20}$ aryl, $C_1$-$C_{20}$ carbonyl, $C_1$-$C_{20}$ amidyl, $C_1$-$C_{20}$ ether, $C_6$-$C_{20}$ aryl, $C_6$-$C_{20}$ heterocyclic containing a heteroatom of N, O, or S; and $B^3$ is a nullity or $C_1$-$C_{20}$ alkyl, $C_4$-$C_{20}$ ether; $C_1$-$C_{20}$ alkyl having a substituent of N, O, or S; $C_1$-$C_{20}$ ester; $C_1$-$C_{20}$ alcohol; $C_1$-$C_{20}$ alkenyl; heteroatom $C_6$-$C_{20}$ aryl, $C_6$-$C_{20}$ heterocyclic containing a heteroatom of N, O or S.

FIG. 1 shows an exemplary substrate structure for detecting lysosomal storage diseases. The structure is composed of a sugar (A) in the form of a glucose or a galactose and an aliphatic group B. Group B is further composed of a linker arm ($B^1$) in the form of a nitrophenyl, a $B^2$ subgroup of a carnitinyl, and a $B^3$ subgroup in the form of an alkyl with carbon length in the range of 12, 14, 16, or 18. A quaternary ammonium cation located on the $B^2$ subgroup provides an ion that avoids the need of further ionization otherwise needed for mass spectrometry detection.

Figure 2:
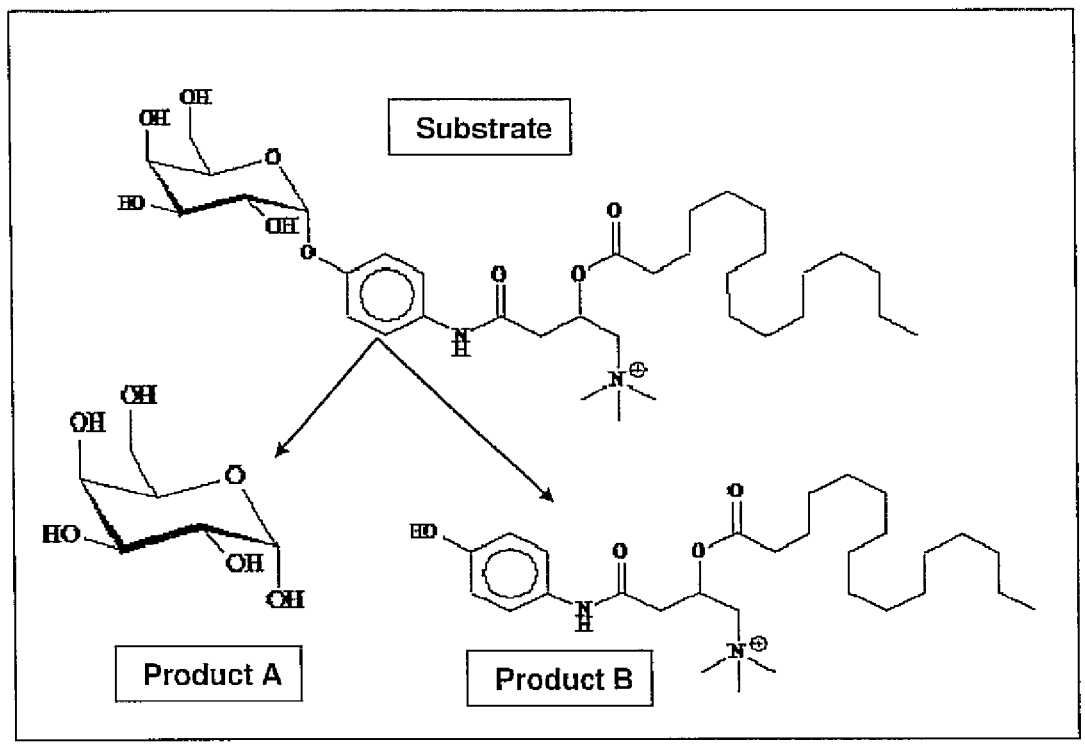
FIG. 2 is a generic enzymatic reaction scheme using an inventive substrate.
Figure 2:
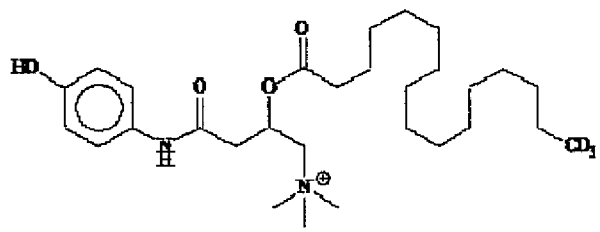

FIG. 2 demonstrates a generic enzymatic reaction using an inventive substrate. Upon specific affinity binding and enzymatic reaction, the substrate is cleaved into two groups, a sugar moiety A and an aliphatic group B. The group B is composed of a nitrophenyl, a carnitinyl, and long-chain alkyl moieties. Both groups are then analyzed by MS/MS. An internal standard is also concurrently subject to the MS/S analysis. The internal standard is an isotopically labeled analog of B with deuterium to replace hydrogen atom(s) on a methyl group.

Figure 3:
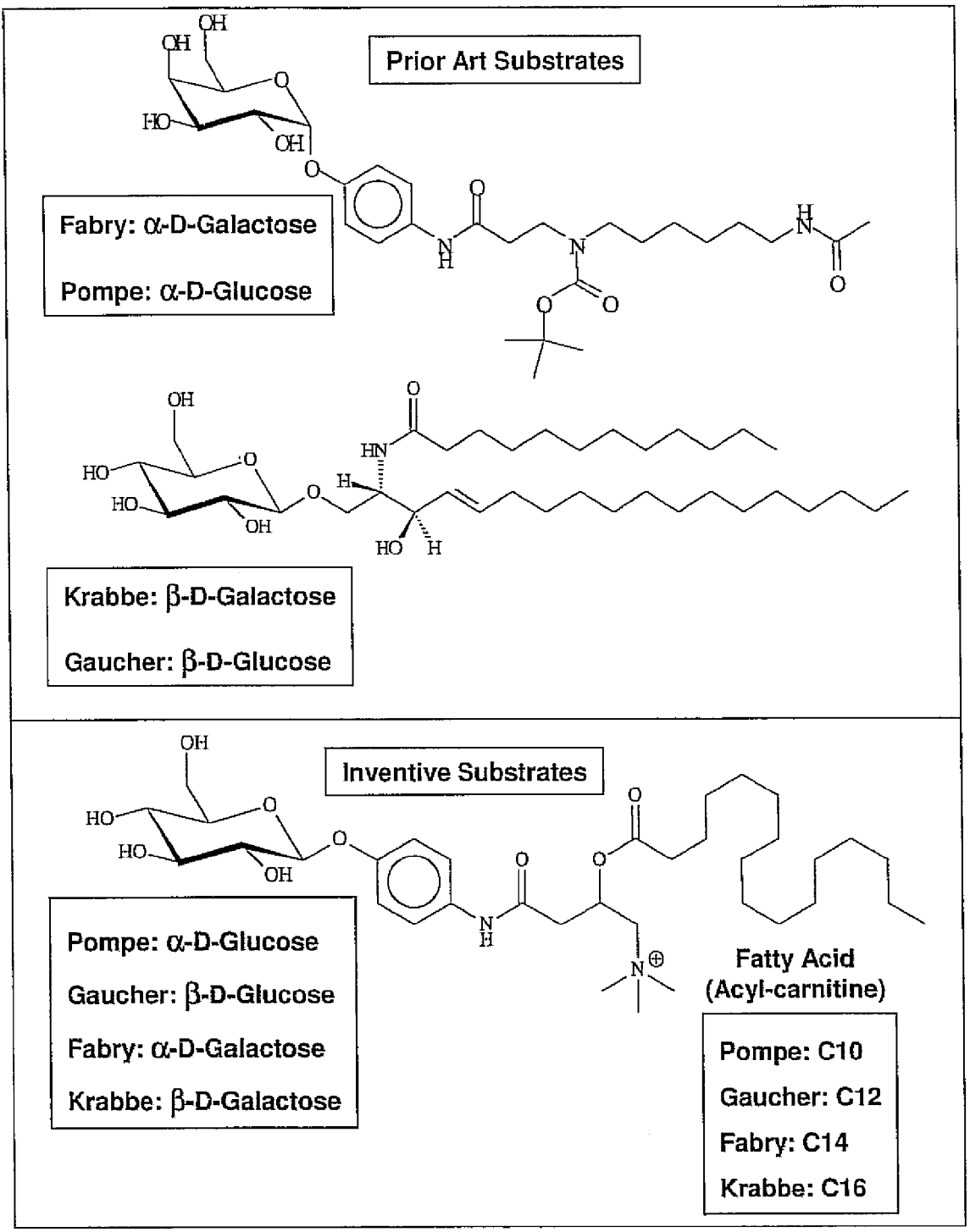
FIG. 3 are major structure differences between an inventive substrate and a prior art substrate.

FIG. 3 illustrates major structure differences between an inventive substrate and a prior art reference substrate known in the art. The differences exist mainly at the long-chain acyl portion wherein in contrast with the prior art substrate, a permanently positively charged quaternary ammonium cation present in the inventive substrate makes itself a "ready-made" ion for the purpose of downstream mass spectrometry analysis. Therefore, no further ionization is needed and hence no loss of signal intensity. Further, in comparison to the prior art substrate, the inventive substrate is chemically less nonpolar. Therefore, a solvent in which the inventive substrate is dissolved does not have to be extremely non-polar nor needs the addition of a detergent. Extremely non-polar solvents such as chloroform are not user friendly and not recommended for ESI-MS/MS. The use of detergent also degrades the functionality of the mass spectrometer as detergents soil the inner parts of the mass spectrometer very rapidly so as to cause a significant decrease in performance. When such reagents are used, one is required to add extra steps to remove these reagents before a sample is subject to MS/MS analysis. To recover the products to be analyzed, prior art uses chloroform or ethylacetate in a liquid-liquid extraction step. To remove the detergent, prior art uses solid phase extractions. Therefore, although it is possible to adapt these procedures in clinical laboratories, the prior art substrates make their use extremely cumbersome if not unpractical.

Figure 4:
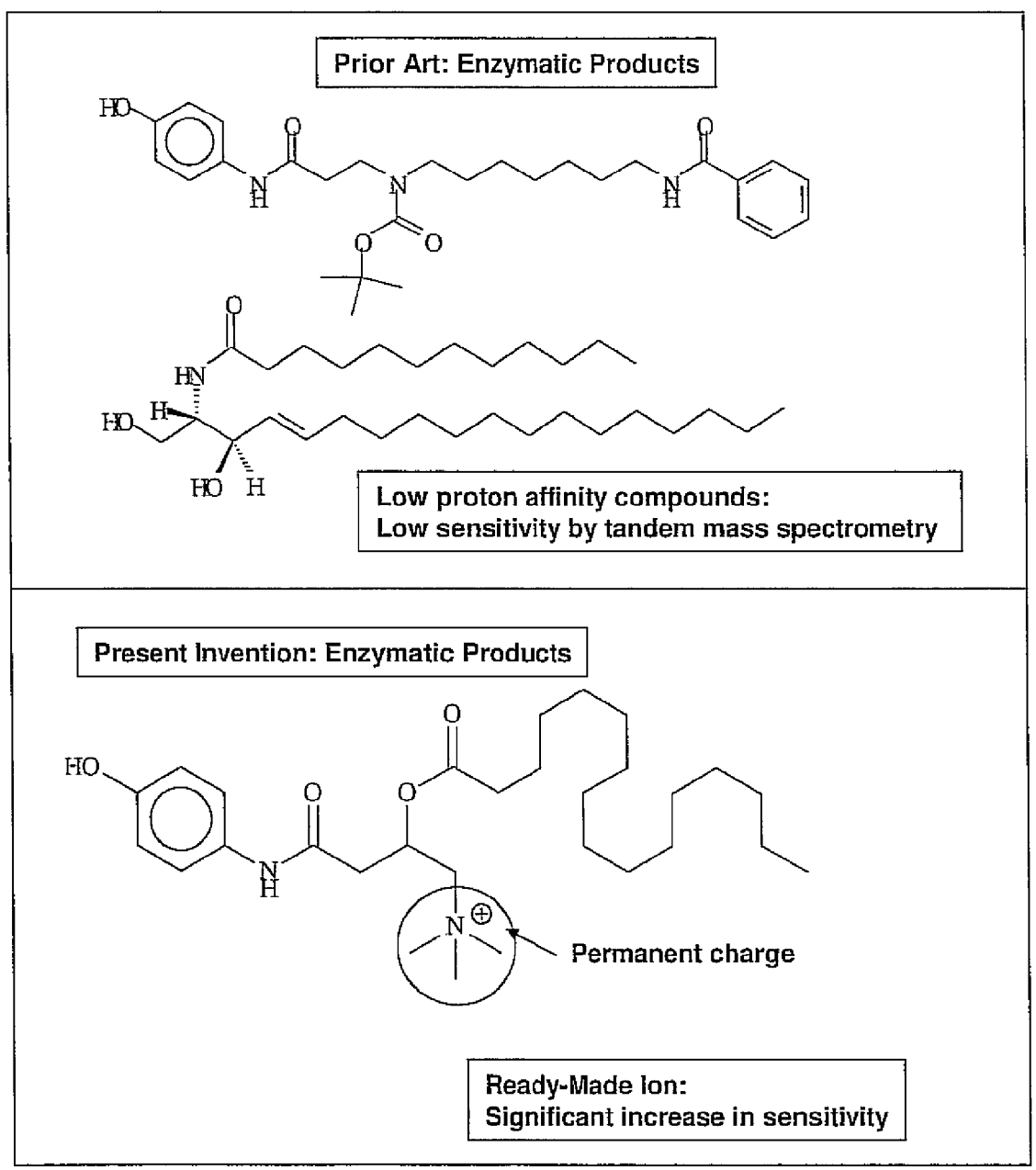
FIG. 4 is a mechanism of increased detection sensitivity rendered by an inventive substrate in comparison to a prior art substrate.

FIG. 4 illustrates a structural difference between an inventive substrate and a prior art substrate. Upon affinity recognition and enzymatic reaction, a part of the inventive substrate, named "enzymatic product", is cleaved. Unlike a product produced from the prior art substrate, the enzymatic product of the present invention has a built-in "Ready-Made" ion (bottom panel) that is permanently positively charged. Any analyte that is introduced in the mass spectrometer must be rendered as an ion to be detected. One of the most important factors affecting sensitivity is ionization efficiency, namely the ease with which the analyte ionizes once exposed to the ion source. Once exposed to the ion source, molecules compete with each other for protons or other charged particles such as metal ions. Molecules with high proton affinities compete more effectively for proton binding and are ionized more efficiently. In the case of an inventive molecule that already possesses a permanent positive charge, the molecule does not require protonation or metal ion adduction; as a result, the enzymatic product of the present invention delivers signal intensity that is in the orders of magnitude better.

Figure 5:
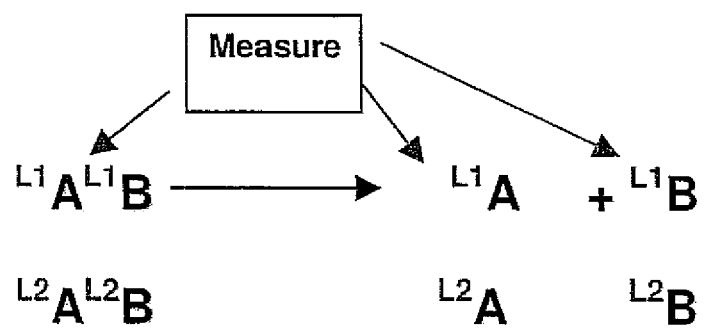
FIG. 5 is an alternative method of detecting enzymatic activities using double labeling of an inventive substrate.

FIG. 5 shows differences in the process of measuring enzyme expression and activity using an inventive method in accordance with the current invention. The inventive method permits a simultaneous measurement of both a decrease in the level of a substrate and an increase in the level of a product. This is advantageous over other methods in the art that only employ the measurement on a product of an enzymatic reaction. Therefore, the inventive method offers higher sensitivity and specificity. For an inventive substrate, both the A portion and the B portion are labeled with a first isotopic tag. For an inventive internal standard for the substrate, both the A portion and the B portion are labeled with a second isotopic tag that is different from the first isotopic tag. Isotopic tag number one and isotopic tag number two are each independently one of the following carbon-12, deuterium, nitrogen-15, phosphor-32, oxygen-17, oxygen-18 and sulfur-34.

Figure 6:
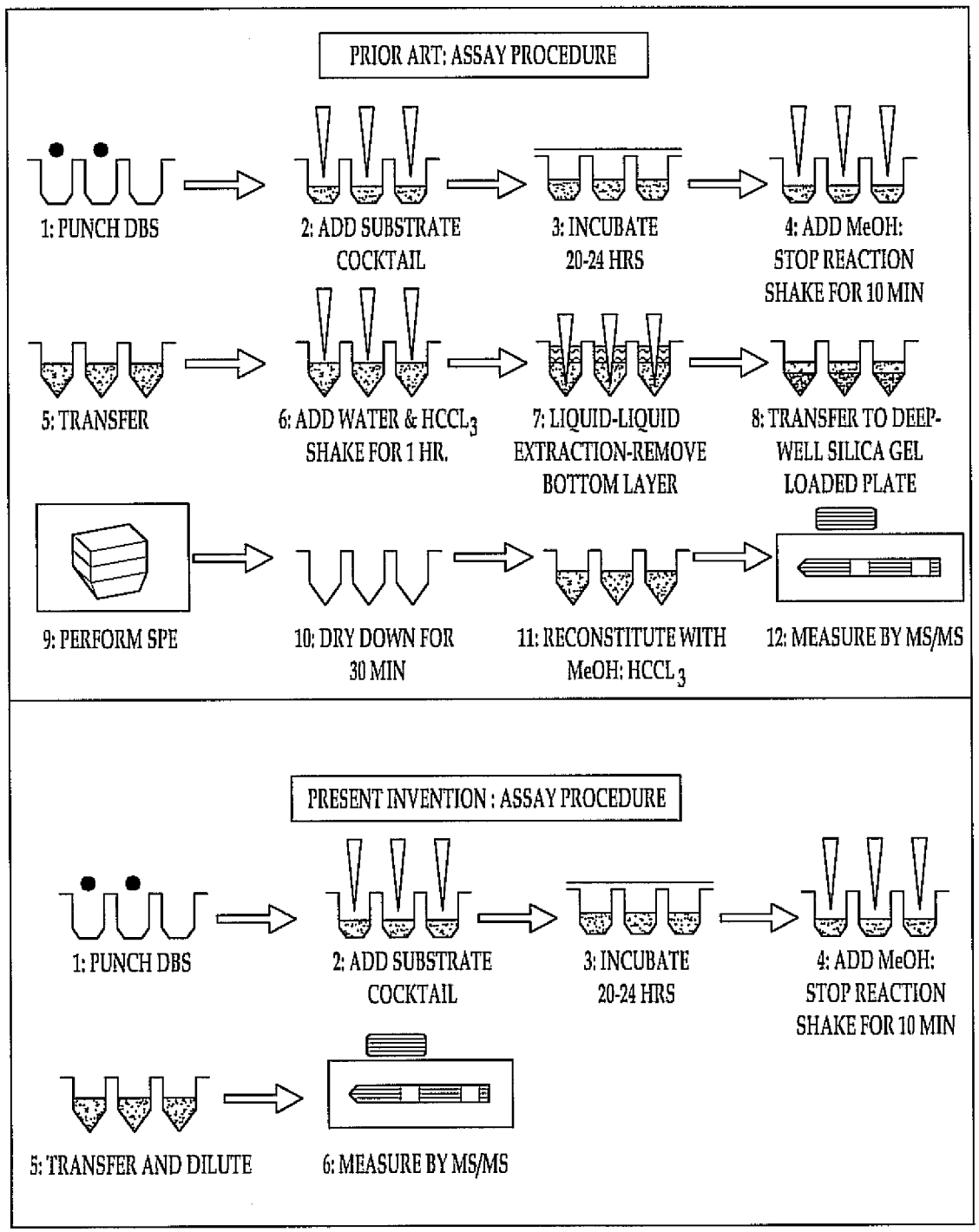
FIG. 6 is an inventive method of detecting enzymatic reactions using mass spectrometry that is advantageous in comparison to a prior art reference method.

FIG. 6 illustrates exemplary inventive methods, with bottom panel depicting detection of enzymatic reactions using mass spectrometry that are advantageous in comparison to a prior art reference method shown at the top of the figure. Compared with the prior art method, the inventive method eliminates many steps that are inherent with the use of non-polar substrates and their relative internal standards. More specifically, the inventive method no longer needs the steps serve to clean up non-polar solvent and or detergents the involvement of which is detrimental to the mass spectrometer. These steps include substrate recovery by a liquid-liquid extraction step and the removal of the detergents by a silica-gel separation step. Since the substrate in accordance with the current invention is less non-polar in contrast to the prior art, a less non-polar solvent such as pure methanol or pure ethanol is operative herein.

Optionally, both the A portion and the $B^1$—$B^2$—$B^3$ portion are each labeled with isotopic tags. The isotopic tags are located on one or more of the atoms including C, H, P, N, O or S.

For detecting Pompe disease, an exemplary sugar moiety is α-D-glucose and an exemplary B portion is 4-aminophenyl-carnitinyl-alkyl chain with $B^3$ of 10-20 carbons in length and preferably of 12 carbons in length. For detecting Gaucher disease, an exemplary sugar moiety is β-D-glucose and an exemplary $B^1$—$B^2$—$B^3$ portion is 4-aminophenyl-carnitinyl-allyl with $B^3$ of 10-20 carbons in length and preferably of 14 carbons in length. For detecting Fabry disease, an exemplary sugar moiety is α-D-galactose and an exemplary B portion is 4-aminophenyl-carnitinyl-alkyl with $B^3$ of 10-20 carbons in length and preferably is of 16 carbons in length. For detecting Krabbe disease, an exemplary sugar moiety is β-D-galactose and an exemplary B portion is 4-aminophenyl-carnitinyl-alkyl with $B^3$ of 10-20 carbons in length and preferably is of 18 carbons in length.

The substrates described herein can be used to detect a lysosomal disorder in an individual. Exemplary enzymes that have deficient activities in lysosomal disorders include acid α-galactosidase A (GLA) for Fabry disease; acid β-glucocerebrosidase (ABG) for Gaucher disease, acid galactocerebroside α-galactosidase (GALC) deficiency for Krabbe disease; and acid α-glucosidase (GAA) for Pompe disease.

When more than one disease is detected simultaneously by combining multiple substrates directed to respective enzymes, the substrates differ not only on the type of the sugar moiety which confers enzyme specificity, but also on the length of the $B^3$ tail moiety. This is particularly important with the use of MS/MS as a detection tool since the differentiated inventive substrate molecules having corresponding differentiated mass index correspond to various enzymes being examined.

Internal standards are employed to measure enzymatic activities in a sample. Internal standards are isotopically labeled to quantitate products of enzymatic reactions. The internal standard is chemically identical to the enzymatic product generated by the action of the enzyme on the inventive enzyme substrate, but carries isotope labels which may include D, $^{13}C$, $^{15}N$, $^{17}O$, $^{18}O$, $^{32}P$, or $^{34}S$, that allow for the isotopically labeled analog to be independently detected by MS techniques.

Internal standards are substantially chemically identical to the corresponding enzymatic products, except that they are differentially isotopically labeled to allow their independent detection by MS techniques. The internal standard can also be differently labeled on both its sugar portion A and the linking portion $B^1$—$B^2$—$B^3$. With mass spectrometry, a simultaneous measurement is provided so that both the decrease of the substrate signal and the increase in products A and $B^1$—$B^2$—$B^3$ are concurrently recorded. This design increases the sensitivity and the specificity of the assay.

The use of a universal substrate cocktail buffer to extract a single dry blood sample per patient for subsequent distribution into multiple assay reactions is advantageous for automatic and high throughput screening because it avoids the need to obtain several sample punches from the same dry blood sample. This also reduces variation caused by inhomogeneous distribution of blood on the filter paper. Extraction efficiency may vary with the different enzymes being analyzed. Particularly, the composition of the inventive universal substrate cocktail buffer is chosen to ensure the highest performance for an enzyme that renders the lowest specific activity of all the enzymes tested.

All reagents including the substrates, the cleaved products, and the internal standards are optionally purified to homogeneity by reverse-phase HPLC and characterized by high-field ESI-MS. Assay components such as enzyme substrates, assay products, and internal standards are processed through a media so as to remove excess buffer components. The removal of the buffer components is particularly suitable for tandem mass spectrometry since electrospray ionization of analytes is expected to be suppressed by the presence of excess buffer components.

The approach described for assaying enzymes using substrate reagents and ESI-MS according to the present invention may be broadly applied. The multiplex techniques may be expanded to assay dozens or more enzymes simultaneously in a single reaction, obviating the need for multiple assays to assist in confirming diagnoses of rare disorders. The method may be used to measure several enzymes simultaneously when evaluating the rate of chemical flux through a specific biochemical pathway or for monitoring biochemical signaling pathways. Because of the high sensitivity of the ESI-MS detection employed, which requires only sub-microgram quantities of the substrate reagents per assay, the synthesis of several hundred substrate reagents on a low-gram scale becomes practical and economical.

EXAMPLES

Example 1

For each sample, a disk of 3 mm diameter is punched from the areas of dried blood on a filter paper into a micro-centrifuge tube or a well of a 96-well microtiter plate. The blood disk is then incubated directly with an assay solution containing a substrate directed to the Fabry disease. The assay solution is prepared by mixing a 10 mM solution of substrate (4-(Hexadecanoyl-DL-carnitineamido)phenyl-α-D-galactopyranoside), a 1 mM solution of the internal standard for the enzymatic product (4-(Hexadecanoyl-DL-carnitine[C16-$d_3$] amido)phenol), a 1 M solution of Acetylgalactosamine, and a 0.4 M solution of sodium acetate pH 4.6 buffer in a 8:1:3:38 ratio. The assay mixture containing the blood disk is incubated for 15 to 24 hours at 37° Celsius with orbital shaking (150 rpm) in a thermostatic air shaker. After the incubation period, an aliquot of pure methanol (without the use of chloroform) is added to each tube or well to terminate the enzymatic reaction. Before going into the mass spectrometer, an aliquot of the incubated aliquot is diluted in pure methanol. For the mass spectrometry analysis, the electrospray source is operated in positive mode, and the ions are detected in the parent ion of 176 scan mode. The amount of enzymatic product is calculated from the ion abundance ratio of the product to the internal standard minus that of a blank.

Figure 7:
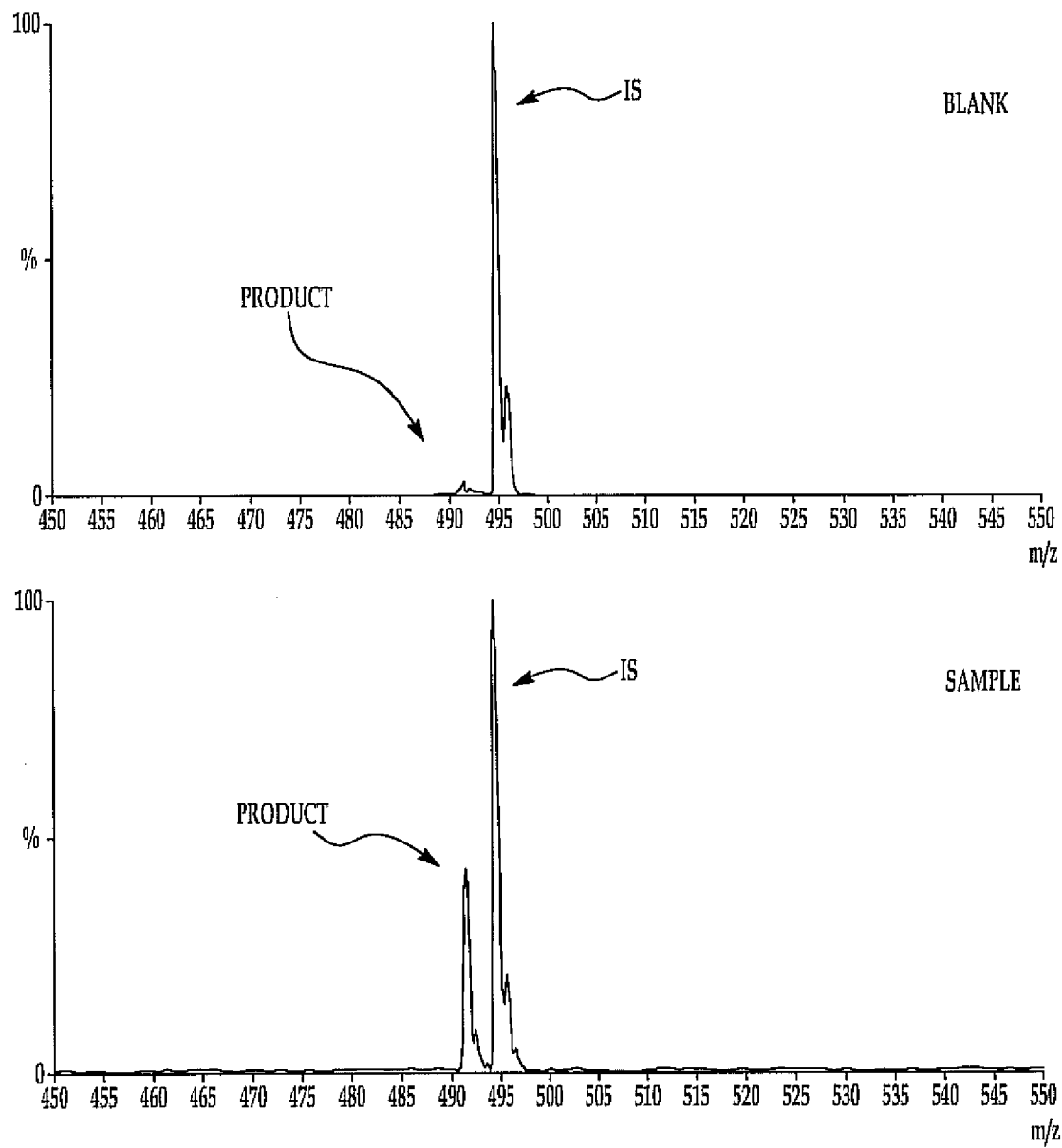
FIG. 7 is a tandem mass spectrum of a substrate sample directed to the Fabry diseases in accordance with the current invention as well as a corresponding blank.

As shown in FIG. 7, the internal standard is detected at m/z of 494.5; and the enzymatic product of the substrate directed to Fabry disease is detected at m/z of 491.5 at a minimal amount in a blank (top) and at a significant amount with the presence of a dried blood sample (bottom).

Example 2

An enzymatic reaction using a substrate directed to Pompe disease and the mass spectrometry analysis thereafter is carried out using the method specified in Example 1 with the following exceptions that sodium citrate was used as buffer. The assay solution for Example 2 was prepared by mixing a buffer solution (0.2 M sodium citrate/sodium phosphate, pH 3.98), a solution of 8 mM Acarbose, a solution of 10 mM substrate (4-Decanoyl-DL-carnitineamido)phenyl-α-D-glucopyranoside), and a solution of 1.0 mM internal standard (4-Decanoyl-DL-carnitine[C10-$d_3$]amido)phenol) in a 93:1:4:2 ratio. The rest of the procedure is as indicated in Example 1.

Figure 8:
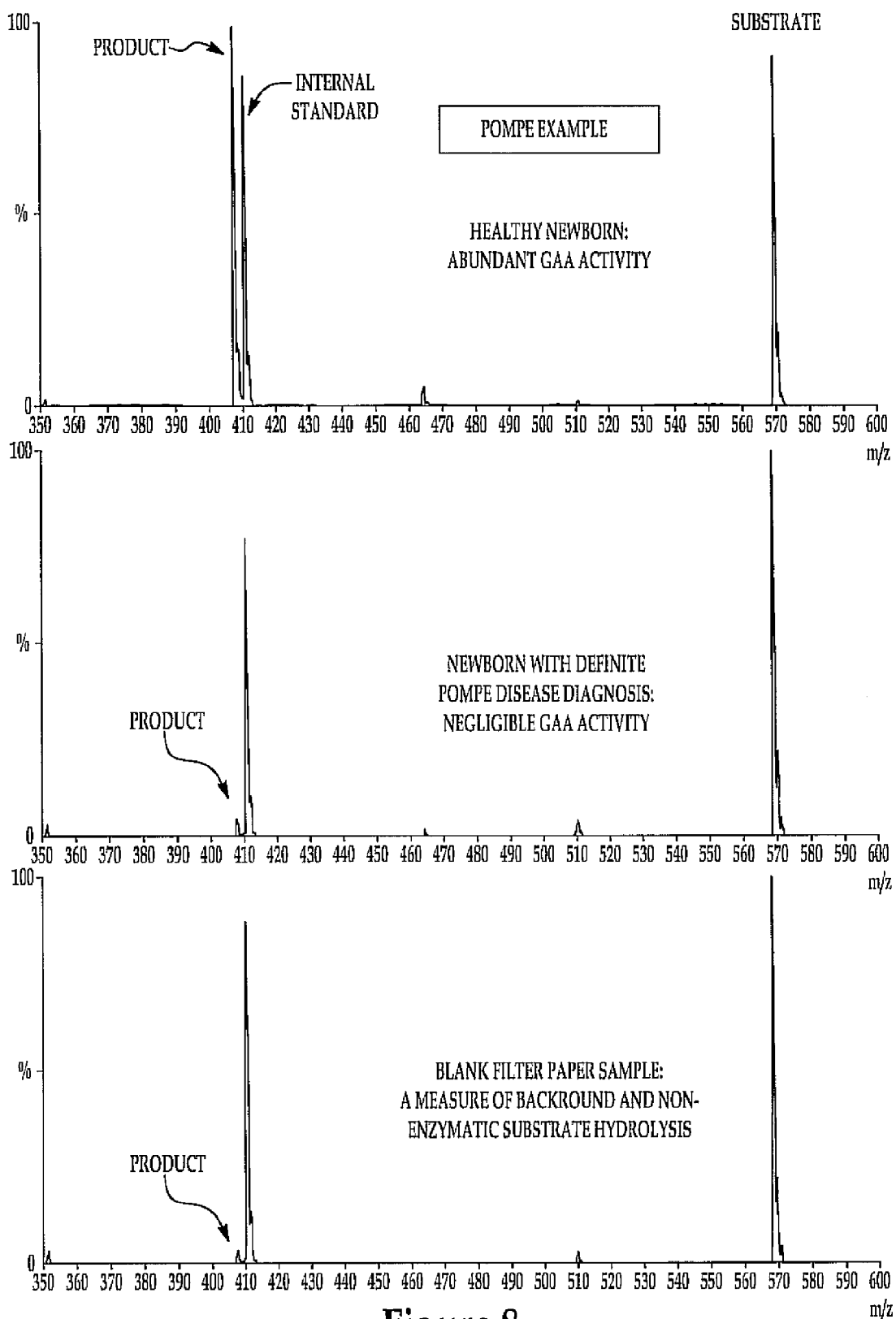
FIG. 8 are tandem mass spectra of an inventive substrate directed to GAA for the Pompe disease in responses to a diseased sample, a healthy sample, or a blank.

FIG. 8 shows an example in which an inventive substrate such as those described in FIG. 1 was synthesized using α-D-glucose as the sugar moiety and thus specific for the lysosomal enzyme GAA (Pompe disease). The allyl chain for this particular example was chosen to contain 10 carbons and thus decanoyl-carnitine was used in the synthesis of the substrate. Similarly, the corresponding internal standard was synthesized using decanoyl-carnitine that had three hydrogens substituted for deuteria on one of the three methyl groups of the carnitinyl moiety. Using this substrate and internal standard, dried blood spot samples from two newborns, one a healthy individual and the other a confirmed positive for Pompe disease, were processed with the method of the present invention as described in FIG. 5. In addition a blank filter paper sample not containing blood was processed following the same procedure as the dried blood spots. The same assay solution containing buffers, substrates, inhibitors and internal standards was used for all three samples. Therefore, all samples received the same concentration of reagents. The final sample solutions were analyzed on a Waters Quattro Micro ESI-triple quadrupole tandem mass spectrometer using a parent ion of 176 scan. The predominant peaks shown in the spectra are those corresponding to the intact substrate, internal standard and corresponding enzymatic product. Because all samples were processed with the same concentration of reagents, the relative abundance between product and internal standards is an indication of the relative enzyme activity between samples.

These spectra clearly show that in the healthy individual there is abundant GAA activity as the conversion of substrate to product is highly noticeable by the abundance of the product relative to the abundance of the internal standard. In contrast, the sample corresponding to the Pompe positive newborn shows negligible GAA enzyme activity as there is no noticeable substrate to product conversion. The small peak corresponding to the product that is noticeable in the spectrum of the Pompe positive newborn is ascribed as background. Examination of the spectrum resulting from the processing of the blank sample reveals also a small peak corresponding to the product. In this case due to the absence of blood in this sample it is clear that the sample processing causes a small degree of non-enzymatic hydrolysis of the substrate. Comparison of the relative abundance of the product/internal standard peaks in the Pompe and blank spectra indicate that the small product peak in the Pompe positive sample is mainly due to non-enzymatic hydrolysis. The fact that there is a small amount of non-enzymatic substrate hydrolysis is not surprising as glycosidic bonds are fairly labile. However, from this example it is clear that the degree of non-enzymatic substrate hydrolysis is negligible once compared to the amount of product conversion in healthy individuals. Therefore, this background should not pose any limitation on the method. These spectra clearly show the utility of the substrates of the present invention as they clearly show that they are clinically specific, sensitive and stable. Further these reagents retain their utility while at the same time allowing significant simplification of the assay.

Example 3

Figure 9:
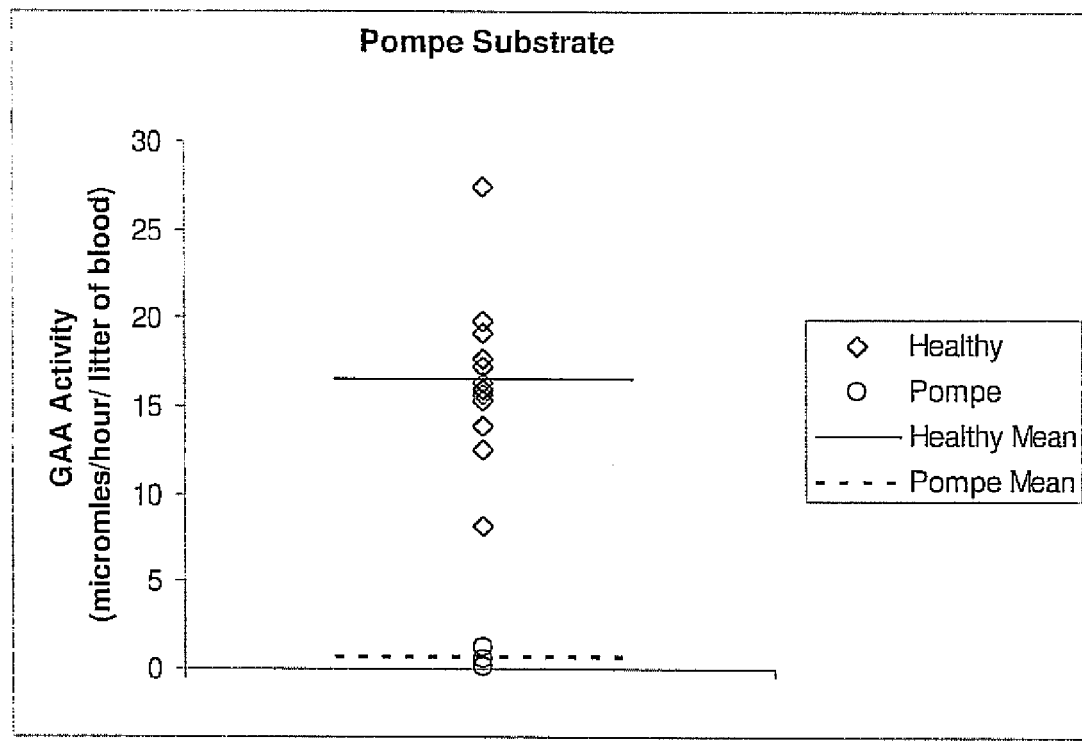
FIG. 9 is a scatter plot indicating differential GAA activities amongst 12 samples from healthy and 3 samples form Pompe positive newborn subjects.

FIG. 9 shows the results of processing dried blood spots samples 12 from healthy and 3 Pompe positive newborns. The reagents and methods used are the same as those described in FIG. 8. Because the internal standards are introduced at known concentrations, it is possible to quantitate the enzyme activities by relating the relative abundance of the product and internal standard to the concentration of the internal standard. This figure shows a scatter plot of the determined enzyme activities in micromoles/hour/liter of blood units for the 15 subjects studied. From this plot it can clearly be seen that there is a clear distinction between the GAA activity of healthy newborns and the activity of affected newborns. The recorded activities of the three Pompe patients are negligible compared to those of the healthy individuals. It is noted that as described in FIG. 8, non-enzymatic hydrolysis does produce a small degree of background. The data presented here are not corrected for background. Still, the difference between healthy and diseased is striking.

Example 4

Figure 10:
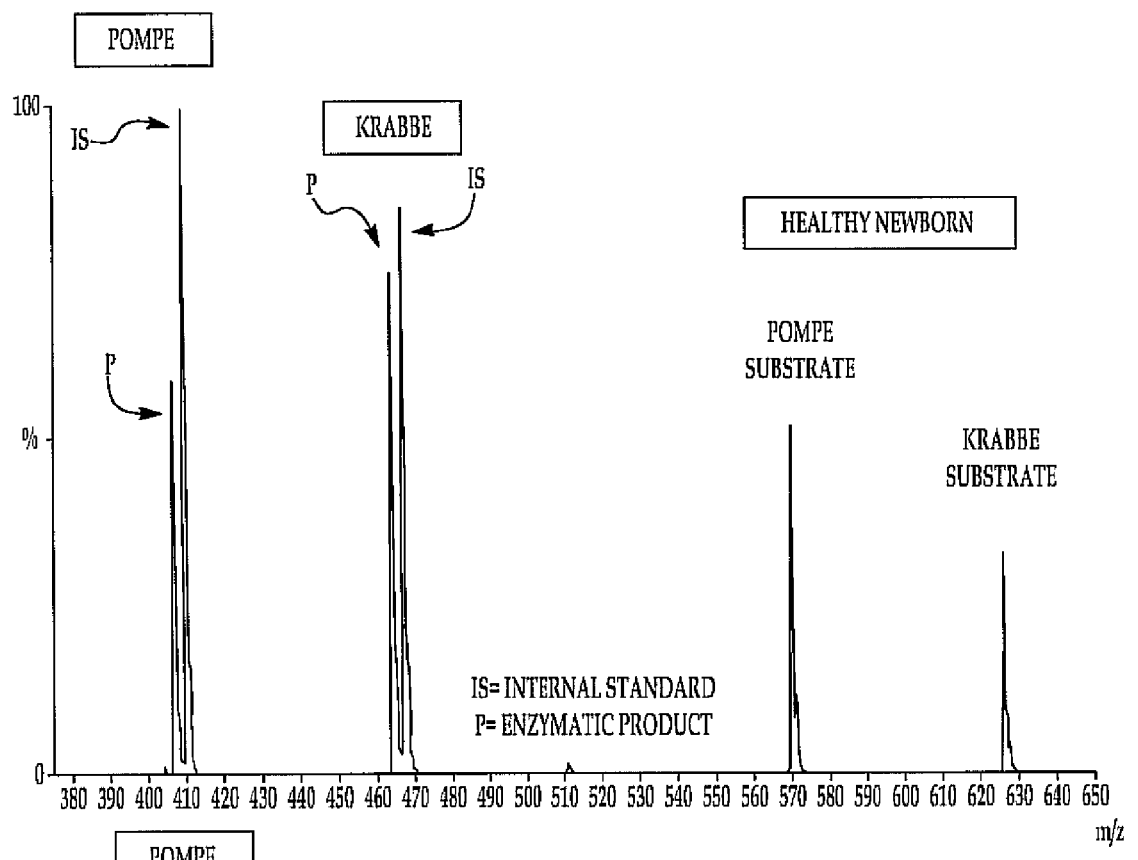
FIG. 10 is an example in which inventive substrates and internal standards are used in a multiplex method by processing the samples using assays solution containing two types of substrates and internal standards.
Figure 10:
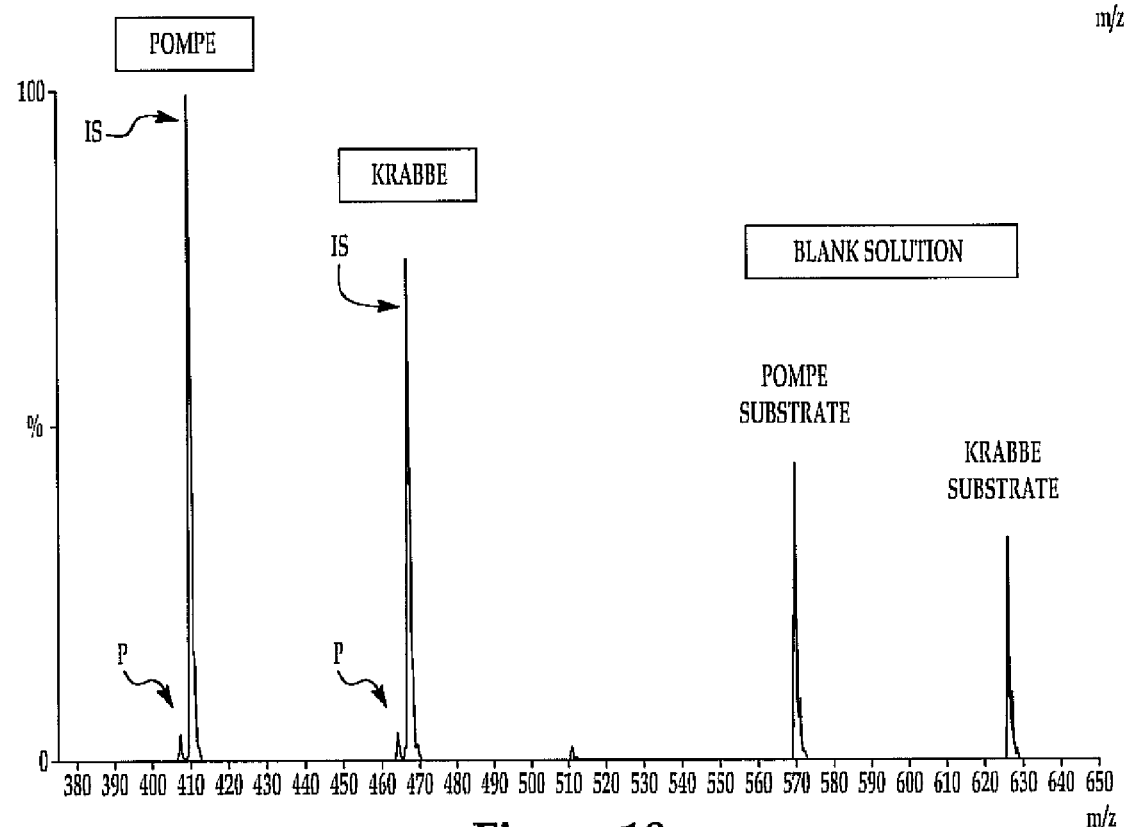

FIG. 10 shows an example in which the inventive substrates and internal standards described in FIG. 1 are used in a multiplex method by processing the samples using assays solution containing two types of substrates and internal standards. On substrate targeting Pompe disease and the other Krabbe disease. The method used is the same as that described in FIG. 8 with the only difference that now substrates for two enzymes are analyzed. The assay solution for this example was prepared by mixing a buffer solution (0.2 M sodium citrate/sodium phosphate, pH 4.0), a 10 mM solution of the Krabbe substrate (4-(Tetradecanoyl-DL-carnitineamido)phenyl-β-Dgalactopyranoside), a 1.0 mM solution of the Krabbe product internal standard (4-(Tetradecanoyl-DL-carnitine[C14-$d_3$]amido)phenol), a 10 mM solution of the Pompe substrate (4-(Decanoyl-DL-carnitineamido)phenyl-α-D-glucopyranoside), a 1.0 mM solution of the Pompe product internal standard (4-(Decanoyl-DL-carnitine[C10-$d_3$] amido)phenol, and a 8 mM solution of Acarbose in a 275:13: 2:8:8:5: ratio. The Pompe substrate is the FIG. 1 substrate prepared with decanoyl-carnitine and the Krabbe substrate is the FIG. 1 substrate prepared with tetradecanoyl-carnitine. The sample used in this example is a dried blood spot sample from a healthy newborn. In addition a blank solution sample not containing blood was processed following the same procedure. In contract to the single enzyme assay described in FIG. 8, the predominant peaks shown in the spectra of FIG. 10 are those corresponding to the intact two substrates added to the solutions, the two internal standard added to the solutions and the two corresponding enzymatic products.

In this example it is seen that the activity of two or more enzymes can be detected simultaneously while retaining good enough sensitivity. This example further demonstrates the utility of the present invention by providing additional simplification to the method as it is possible to consolidate sample preparations.

Example 5

Figure 11:
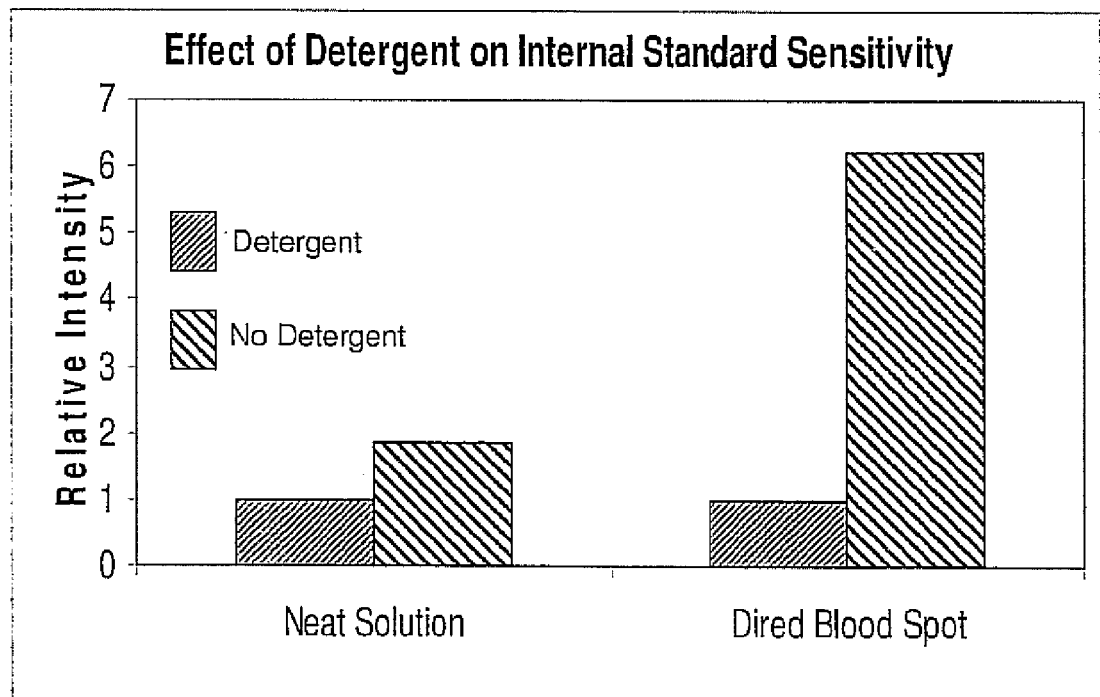
FIG. 11 is the effect of detergent on the sensitivity of the internal standards from the present invention.

FIG. 11 shows the effect of detergent on the sensitivity of the internal standards from the present invention. This data is used to exemplify the impact of detergents on the overall sensitivity of the assay. Despite the fact that the internal standards are already charged prior to the mass spectrometry analysis, ion suppression can still play a role in their sensitivity. Detergents are known to cause significant ion suppression. In this case, the sensitivity of the internal standards in neat solutions (pure methanol) with and without detergents is shown. In addition, the sensitivity of the internal standards in solutions containing extracted dried blood spots with and without detergents is also shown. In this example, internal standards of several alkyl chain lengths and containing α- and β-glucose and galactose were dissolved in either the neat solution or were dissolved in the assay solution with which dried blood spots were extracted and processed as described in FIGS. 8 and 10. In this example an aliquot of each solution type contained no detergent while another did. Therefore, the only difference in these paired samples was the presence or absence of detergent. The paired samples were analyzed by tandem mass spectrometry. The signal intensity of the internal standards in each sample was recorded and used to generate an average relative sensitivity. The plot shows the normalized averaged intensities for samples processed with and without detergent. It is evident that detergent does cause ion suppression a seen by the lower intensities in samples containing detergent. This figure also indicates that the impact of detergent is much more pronounces in samples containing complex matrices such as blood and thus highlights the need for avoiding the use of such substances in tandem mass spectrometry assays.

Example 6

Figure 12:
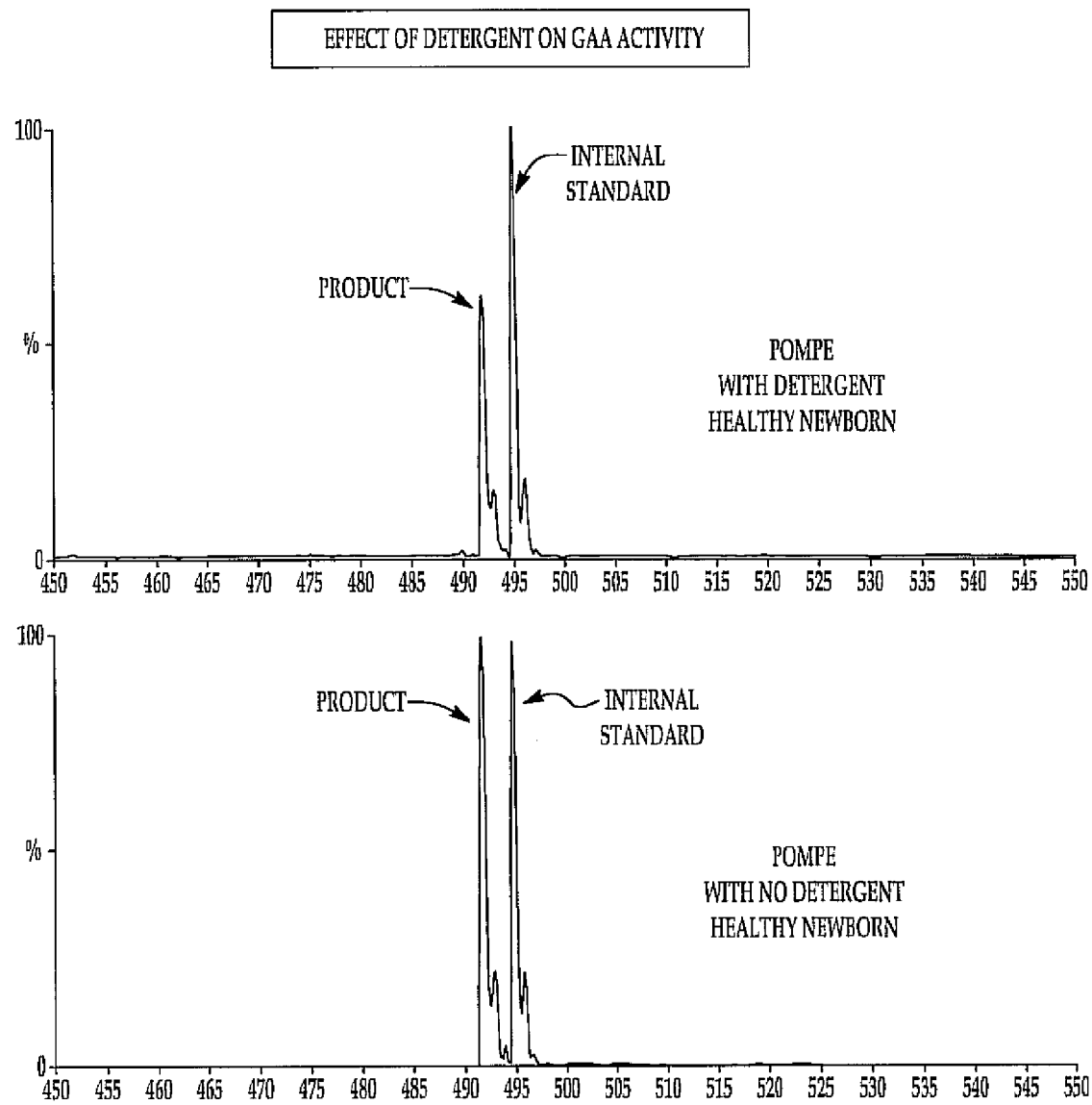
FIG. 12 is differential tandem mass spectrum of an inventive substrate sample directed to the Pompe disease with or without the presence of detergent.

FIG. 12 shows an example in which the effect of detergent on the enzyme activity is analyzed. In this example, a substrate of this invention (FIG. 1) containing α-D-glucose and a 16-carbon fatty acid chain was used to process dried blood spots according to the procedure described in FIG. 8. For this example assay solutions with and without detergent were made. The detergent-free assay solution consisted of a mixture of buffer, substrate, internal standard, and Acarbose at a 93:4:2:1 ratio (the concentration of the individual buffers and reagent solutions are as indicated in FIG. 8). The detergent-containing assay solution consisted of a mixture of the buffer, substrate, internal standard, Acarbose and Triton X-100 at a 93:4:2:1:0.05 ratio. In order to test the effect of detergent, parallel samples from the same patients were prepared according to the above method with and without detergent. FIG. 11 demonstrates that detergent degrades the sensitivity of the assay. However, the question remained on whether the detergent has any impact on enzyme activity. The spectra shown in FIG. 12 clearly show that detergent does have an effect on the enzyme activity evaluated. In this case the absence of detergent in the assay solution enhances the rate of enzymatic activity as demonstrated by the more elevated abundance of the product relative to its corresponding internal standard for the sample processed with no detergent. This example further reaffirms the utility of the present invention by demonstrating that not only the method can be simplified, but that in doing so the sensitivity of the assay is enhanced by reducing ion suppression and enhancing the activity of the targeted enzymes.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A substrate for mass spectrometric detection of a lysosomal storage disorder having the formula:

A—(B1—B2—B3)     (I)

where A is D-glucose or D-galactose, B1 is $C_1$ alkyl or a C6 aryl having a N or O substituent extending from the ring, B2 is an amidyl terminating with a quaternary ammonium or carnitinyl, and B3 is an alkenyl alcohol with a carbon length of 12 to 20 or $C_2$-$C_{20}$ alkyl having a substituent of O present as a carbonyl, where B1 is covalently associated with A by a glycosidic bond;

said B1 is covalently associated with said A and said B2, and said B3 is covalently associated with said B2.

2. The substrate of claim 1 wherein A and ($B^1$—$B^2$—$B^3$) are separable by an action of an enzyme.

3. The substrate of claim 1 wherein A and ($B^1$—$B^2$—$B^3$) portions each include a stable secondary prevalence isotope of an element.

4. The substrate of claim 3 wherein said stable secondary prevalence isotope in each occurrence is selected from the group consisting of $^2$D, $^{13}$C, $^{15}$N, $^{17}$O, $^{18}$O, $^{31}$P and $^{34}$S.

5. A substrate for mass spectrometric detection of the Krabbe disease having formula of A—($B^1$—$B^2$—$B^3$) wherein group A is β-D-galactose, $B^1$ is $C_1$ alkyl, $B^2$ is an amidyl terminating with a quaternary ammonium, and $B^3$ is an alkenyl alcohol with a carbon length of 12 to 20, where A and B1 are associated by a glycosidic bond.

6. A substrate for mass spectrometric detection of the Gaucher disease having formula of A—($B^1$—$B^2$—$B^3$) wherein group A is β-D-glucose, $B^1$ is $C_1$ alkyl, $B^2$ is an amidyl terminating with a quaternary ammonium, and $B^3$ is an alkenyl alcohol with a carbon length of 12 to 20,
where A and B1 are associated by a glycosidic bond.

7. A commercial package comprising as active ingredients a substrate of Formula I of A—($B^1$—$B^2$—$B^3$) according to claim 1; an internal standard of formula ($B^1$—$B^2$—$B^3$)' having a stable secondary prevalence isotope molecular weight different than ($B^1$—$B^2$—$B^3$); and instructions for detecting activity of an enzyme in a sample by mass spectrometric analysis.

8. A process for mass spectrometric analysis of an enzyme comprising:
   contacting said enzyme with said substrate of Formula I of A—($B^1$—$B^2$—$B^3$) according to claim 1 to generate a cleavage product ($B^1$—$B^2$—$B^3$) having a cleavage product molecular weight upon enzymatic reaction;
   providing an internal standard ($B^1$—$B^2$—$B^3$)' with said substrate where ($B^1$—$B^2$—$B^3$)' has at least one stable secondary prevalence isotope of molecular weight different than the cleavage product molecular weight and $B^1$, $B^2$, and $B^3$ of ($B^1$—$B^2$—$B^3$)' according to claim 1; and
   quantifying mass-to-charge ratio between said cleaved product and said internal standard using mass spectrometric analysis.

9. The process of claim 8 wherein said enzyme is selected from the group consisting of acid α-galactosidase A, acid β-glucocerebrosidase, galactocerebroside α-galactosidase, acid sphingomyelinase, and acid α-glucosidase.

10. The process of claim 8 wherein said cleavage product of ($B^1$—$B^2$—$B^3$) is structurally identical to said internal standard of ($B^1$—$B^2$—$B^3$)'.

11. A process for mass spectrometric analysis of an enzyme comprising:
   labeling a first substrate of a Formula I of A—($B^1$—$B^2$—$B^3$) according to claim 1 with isotopic tag L1 to form a first substrate $^{L1}$(A)—$^{L1}$($B^1$—$B^2$—$B^3$);
   labeling a second substrate of Formula I of A—($B^1$—$B^2$—$B^3$) according to claim 1 with isotopic tag L2 to form a second substrate $^{L2}$(A)—$^{L2}$($B^1$—$B^2$—$B^3$) wherein said isotopic tag L2 is different from said isotopic tag L1;
   combining said first substrate $^{L1}$(A)—$^{L1}$($B^1$—$B^2$—$B^3$) and said second substrate $^{L2}$(A)-$^{L2}$($B^1$—$B^2$—$B^3$) with said enzyme in a housing wherein said first substrate $^{L1}$(A)—$^{L1}$($B^1$—$B^2$—$B^3$) is cleaved by said enzyme to form $^{L1}$A and $^{L1}$($B^1$—$B^2$—$B^3$), wherein said second substrate $^{L2}$(A)—$^{L2}$($B^1$—$B^2$—$B^3$) is cleaved by said enzyme to form $^{L2}$A and $^{L2}$($B^1$—$B^2$—$B^3$); and
   quantifying a decrease of said first substrate $^{L1}$(A)—$^{L1}$($B^1$—$B^2$—$B^3$) and said second substrate $^{L2}$(A)—$^{L2}$($B^1$—$B^2$—$B^3$) and an increase of said $^{L1}$(A), $^{L1}$($B^1$—$B^2$—$B^3$), $^{L2}$(A), and $^{L2}$($B^1$—$B^2$—$B^3$).

12. The process according to claim 11 wherein said housing is test tube, a test vial, or a multi-well microplate.

13. The process according to claim 11 wherein said measuring is accomplished by mass spectrometry.

14. The process according to claim 11 wherein said enzyme is selected from the group consisting of acid α-galactosidase A, acid β-glucocerebrosidase, galactocerebroside α-galactosidase, acid sphingomyelinase, and acid α-glucosidase, said enzyme collected in a sample from an individual and abnormal activity being associated with a first lysosomal storage disease.

15. The process according to claim 14 further comprising a second enzyme in the sample associated with a second lysosomal storage disease.

\* \* \* \* \*